United States Patent [19]
Bianco

[11] Patent Number: 6,051,566
[45] Date of Patent: Apr. 18, 2000

[54] ANTI-REACTIVE ANTI-ASTHMATIC ACTIVITY OF NON-STEROIDAL ANTI-INFLAMMATORY DRUGS BY INHALATION

[75] Inventor: Sebastiano Bianco, Milan, Italy

[73] Assignee: B.S.D. Bio Science Development SNC DI Omini C. & Zuccari G., Milan, Italy

[21] Appl. No.: 09/032,973

[22] Filed: Mar. 2, 1998

Related U.S. Application Data

[63] Continuation of application No. 08/906,477, Aug. 5, 1997, abandoned, which is a continuation of application No. 07/832,164, Feb. 6, 1992, abandoned.

[30] Foreign Application Priority Data

Feb. 9, 1991 [EP] European Pat. Off. .............. 91101818

[51] Int. Cl.$^7$ .......................... A61K 31/60; A61K 31/54; A61K 31/40; A61K 31/19
[52] U.S. Cl. ...................... 514/165; 514/226.5; 514/420; 514/570
[58] Field of Search .................................... 514/165, 570, 514/420, 226.5

[56] References Cited

U.S. PATENT DOCUMENTS 5,244,899  9/1993  Mueller et al. .......................... 514/216

OTHER PUBLICATIONS

The Merck Index, Eleventh edition, pp. 1441, cit#9080, 1989.
Martindale The Extra Pharmacopoeia, 28th ed., pp. 234–282, 1982.
Carnimeo et al., *Allergol. Et. Immunopathol.*, 9(1)(1–8), 1981.
Pasargiklian et al., *Respiration* 34:79–91 (1977).
F. Egede, "Fatalt forlobende astmatisk reaktion efter keptoprofen (Alreumat®), (Orudis®), " *Ugeskrift for Leager*, 141(17): 1151–1152 (1979).
M. Robuschi et al., "Tollerabilita del Tenoxicam Negli Asmatici Aspirino–Sensibili," *Giornale Italiano della Malattie del Torace*, 40(1): 17–23 (1986).
A. Szczeklik, "Anti–cyclo–oyxgenase Agents and Asthma," *J. Asthma*, 20(S–1): 23–29 (1983).
A. Szczeklik, "Analgesics Allergy and Asthma," *Drugs*, 32(Suppl. 4): 146–163 (1986).

A. Szczeklik et al., "Asthma and Anti–inflammatory Drugs: Mechanisms and Clinical Patterns," *Current Therapeutics*, 24(9): 11–19 (1983).
A.J. Fairfax et al., "The Late Reaction Following Bronchial Provocation with House Dust Mite Allergen. Dependence on Arachiodonic Acid Metabolism," *Clin. Exp. Immunol*, 52: 393–398 (1983).
A. Szczeklik, "Analgesics, Allergy and Asthma," *Br. J. Clin. Pharmac.*, 10(Suppl. 2): 401S–405S (1980).
J. Kreukniet, "Inhalatiecorticosteroiden bij Astma," *Farmacotherapie*, vol. 132, (1989), pp. 177–179.
H. Gong et al., "Alcohol–induced Bronchospasm in an Asthmatic patient," *Cardiopulmonary J. Chest*, vol. 80, (1981), pp. 167–173.
M. Robuschi et al., "Inhaled Frusemide is Highly Effective in Preventing Ultrasonically Nebulised Water Bronchoconstriction, " *Pulmonary Pharmacology*, vol. 1, (1989), pp. 187–191.
M.L. Kowalski et al., "Clinical Efficacy of Aspirin in 'Desensitized' Aspirin Sensitive Asthmatics," *Eur. J. Rerspir. Dis.*, vol. 69, (1986), pp. 219–225.
S. Bianco et al., "Bronchial Response to Nonsteroidal Anti–inflammatory Drugs in Athmatic Patients," *Prog. Biochem. Pharmacol.*, vol. 20, (1985), pp. 132–142.
J.T. Chui, "Improvement in Aspirin–sensitive Asthmatic Subjects After Rapid Aspirin Densitization and Aspirin Maintenance (AdAM) Treatment, " *J. Allergy Clin. Immunol.*, vol. 71, (1983), pp. 560–567.
A.J. Farifax, "Inhibition of the Late Asthmatic Response to House Dust Mite by Non–steroidal Anti–inflamatory Drugs," *Prostaglandins Leuhotrienes and Medicine*, vol. 8 (1982), pp. 239–248.

*Primary Examiner*—Raymond Henley, III
*Attorney, Agent, or Firm*—Finnegan, Henderson, Farabow, Garrett & Dunner, L.L.P.

[57] ABSTRACT

Non-steroidal anti-inflammatory drugs proved to be effective drugs for combating and preventing asthma if administered by inhalation. Useful are for instance acetylsalicylic acid, and indomethacin, and ketoprofen, and tenoxicam. Suitable pharmaceutical compositions for inhalation are aerosols with a particle size of from 0.5 µm to 7 µm which enter the compartments of the lungs. Aqueous or aqueous-organic solutions or suspensions can be nebulized in combination with propelling agents, or mixtures of powders with microfine drugs can be administered using inhalers. These pharmaceutical compositions may comprise appropriate additives, in order to improve their relevant pharmaceutical properties.

20 Claims, 11 Drawing Sheets

ANTI-REACTIVE ANTI-ASTHMATIC ACTIVITY OF NON-STEROIDAL ANTI-INFLAMMATORY DRUGS BY INHALATION

This is a continuation of U.S. Ser. No. 08/906,477 filed Aug. 5, 1997, now abandoned, which is a continuation of U.S. Ser. No. 07/832,164 filed Feb. 6, 1992, now abandoned.

The invention relates to the use of non-steroidal anti-inflammatory drugs for the production of an anti-reactive anti-asthmatic drug to be administered by inhalation; it relates also to non-steroidal anti-inflammatory drugs as medicaments to be inhaled for combating and preventing asthma.

Bronchial inflammation plays a key role in the current views on the pathogenetic mechanisms of bronchial asthma (Am Rev Respir Dis 1987; 138:740–51). Despite relatively large experimental evidence for the involvement of arachidonic acid metabolites in these mechanisms (J Appl Physiol 1989, 66:578–583), several previous attempts to influence the bronchial responses using anti-inflammatory drugs with cyclooxygenase inhibitory activity have failed to show a clinically significant and consistent effect of these drugs in asthma (J Allergy Clin Immunol 1983, 71:245–249). One of the limiting factors of the effect of these drugs on bronchial responses might be a scarce availability of these drugs in the lung following systemic administration. Indeed, a significant reduction of the bronchial response to ultrasonically nebulized water (UNW) in asthmatics after oral administration of relatively high doses of aspirin was observed (Progress in Biochemical Pharmacology (Karger, Basel) 1985, 20:132–142.2, and Allergologie, deuxieme edition, J Charpin ed, Flammanion publ., Paris 1986, p 683–693, and Respiration 1988, 54(suppl 1):100–107). Since a similar dose of the chemically related compound, sodium salicylate, which is devoid of inhibitory activity on cyclooxygenase, has no effect (L'acetilsalicilato di lisina ma non il salicilato protegge dal broncospasmo da H20. III Conferenza Italiana di Medicina Respiratoria, Milano 1990, Abstract book p 181), it can be concluded that cyclooxygenase inhibitors play a role in the therapeutic control of asthma, but relatively high doses have to be administered to afford a significant protective effect. Unfortunately, chronic treatment with such oral doses of NSAIDs causes an unacceptable rate of side effects, as indicated by two controlled studies available on the effect of treatment with high doses (1.3 to 2.6 g daily) of aspirin in asthmatics (J Allergy Clin Immunol 1984, 73:500–507; and J Allergy Clin Immunol 1990, 85:59–65).

The aim of this invention was to make a breakthrough in the treatment of asthma with acceptable doses of a non-steroidal medicament.

This was accomplished by inhaling a non-steroidal anti-inflammatory drug (NSAID), preferably acetylsalicylic acid (ASA), but also indomethacin, ketoprofen and tenoxicam.

Part of this invention is also a non-steroidal anti-inflammatory drug for application by inhalation in combating asthma, non-steroidal anti-inflammatory drugs of particular interest are acetylsalicylic acid, indomethacin, ketoprofen and tenoxicam.

The studies of this invention clearly show that inhaled NSAIDs, particularly lysine-acetylsalicylate (L-ASA), the soluble form of ASA, induce a remarkable attenuation of the bronchial responses to both non-specific (UNW) and specific (immediate and late reactions to allergen) stimuli in asthmatics in the absence of side-effects.

Suitable pharmaceutical compositions for inhalation are aerosols with a particle size of from 0.5 $\mu$m to 7 $\mu$m which enter the compartments of the lungs. Aqueous or aqueous-organic solutions or suspensions which can be nebulized in combination with propelling agents, such as fluoro chloro hydrocarbons, fluorinated hydrocarbons, dimethyl ether, propane, butane, nitrogen, carbon dioxide, $N_2O$, or mixtures of powders with microfine drugs, which can be administered using inhalers are particularly suitable. These pharmaceutical compositions may comprise appropriate additives, such as surface active substances, for instance phospholipids, sorbitane esters, polyoxy sorbitane esters, or oleic acids, alcohols and polyols such as ethanol, glycerol, poly ethylene glycol, glucose, mannitol, sorbitol, in order to improve their relevant pharmaceutical properties.

PATIENTS AND METHODS

A) Studies on non-specific bronchial hyperreactivity

Patients

Clinically stable patients with either allergic or non-allergic asthma with a baseline forced expiratory volume at 1 second ($FEV_1$) greater than 70% of predicted, who were free of viral or bacterial respiratory infection for at least 4 weeks were studied. None of the patients had a history of L-ASA induced asthma. All the patients were either treated with inhaled beta2-stimulants or with inhaled beta2-stimulants and topical steroids, that were withheld for 10 hours before administration of the test drug (J Allergy Immunol 1975; 56:323–327).

Methods

Bronchial reactivity to ultrasonically nebulized water (UNW) was measured as previously described (Eur J Respir Dis 1980 (suppl 106):41–9; and Pulmonary Pharmacology 1989, 1:187–191). Each subject inhaled increasing doubling doses of UNW produced by an ultrasonic nebulizer (DeVilbiss Ultra-neb 99) set to an output of 2 ml/min. The subjects were instructed to breath at tidal volume, keeping the mouthpiece between their teeth with the mouth semi-opened. Doubling doses of UNW were administered by progressively increasing the time of exposure from 30" (1 ml) to 240" (15 ml) and if necessary for further 240" setting the output to 4 ml/min (31 ml). Respiratory function was monitored after each dose, until a $FEV_1$ decrease of 20% or greater compared to baseline was observed. In the cases where specific airway resistance (sRaw) was measured, this was done during normal breathing using a constant-volume body plethysmograph with a closed bag system to condition air to body temperature pressure saturation (BTPS) (Fenyves & Gut, Basel, Switzerland) before and after pretreatment, and immediately after each test. $FEV_1$ was measured using a spirometer (Vitalograph). The best value of the first 3 technically satisfactory spirograms was chosen for analysis. The dose of UNW causing a 20% $FEV_1$ decrease ($PD_{20}$) was then calculated by interpolation on the cumulative dose-response curve.

Study design

To test the effect of L-ASA on UNW-induced bronchoconstriction, in a group of 7 subjects with a positive response to a preliminary UNW challenge, the test was repeated twice, with intervals of 3–7 days between treatments which were either 5 ml of L-ASA (180 mg/ml in saline corresponding to 100 mg/ml of ASA) or placebo, according to a randomized protocol, by means of a nebulizer set to run to dryness in about 30'. The UNW challenge was repeated 30' after treatment and once more the next day, 24 hours after treatment. The clinical characteristics of the patients in this group are reported in table I.

In a second group of 6 patients, whose clinical characteristics are reported in table II, the effect of inhaled indomethacin was tested according to a protocol identical to the previous one, except that pre-treatment consisted of the inhalation of either 5 ml of indomethacin 5 mg/ml for 25' or the appropriate placebo and the fog challenge was not repeated 24 hours after treatment. The test was repeated a third time in three of these patients after pretreatment with a higher dose of indomethacin (5 ml at 10 mg/ml nebulized in 25').

In four separate patients, with comparable clinical characteristics to the previous group, the effect of the two NSAIDs, ketoprofen and tenoxicam, on the immediate bronchial response to UNW was investigated in a pilot study. This study protocol was identical to the previous study, except that L-ASA was substituted by a solution of either ketoprofen 10 mg/ml or tenoxicam 2 mg/ml. The effect of tenoxicam was tested in three, and ketoprofen in two subjects.

Additionally, in a third group of patients, whose clinical characteristics are reported in Table III, the effects of tenoxicam on the immediate bronchial response to UNW was investigated in seven patients. The study protocol was identical to the previous ones except that 5 ml of a 4 mg/ml solution was nebulized over a period of 30 minutes in this test.

In a fourth group of five patients, whose clinical characteristics are reported in Table IV, the effects of Ketoprofen was investigated on the immediate bronchial response to UNW. Again the same protocol was used as in the previous studies except that 7 ml of a 7.14 mg/ml solution was nebulized over a period of 40 minutes in this study. The test was performed 40 minutes after the end of nebulization.

B) Allergen specific bronchial challenge

Patients

Volunteers with allergic asthma who had an early obstructive response after specific allergen bronchial challenge were recruited among patients attending an allergy clinic. All the patients had a clinical history of allergic asthma and/or rhinitis, showed a positive immediate skin reaction to the clinically relevant allergen, were either asymptomatic or had very mild respiratory symptoms, had a baseline $FEV_1$ over 70% of predicted and had been free of respiratory infections for at least 4 weeks. All the patients were either untreated or under occasional topical therapy, that was withheld as described for UNW test. Patients allergic to pollen were investigated outside the pollen season.

Methods

Specific bronchial challenge was performed as reported in N Engl J Med 1989, 321:1069–1073.

In a preliminary bronchial challenge, the allergen (Frazioni Alfa, Dome/Hollister-Stier, Bayropharm Italiana, Milano, Italy) was administered by a dosimeter (MEFAR, Bovezza, Italy). The apparatus was manually operated by the investigator and was set to deliver 3.7 µl/puff in 0.6 seconds, with a pause of 6 seconds between puffs.

The allergen was dissolved in normal saline at a concentration of 40 Activity Units (AU) per ml for doses up to 2.4 AU (corresponding to a delivered dose of 0.15 AU/puff), or 160 AU/ml for doses up to 9.6 AU (0.6 AU/puff), or 320 AU/ml (1.2 AU/puff) for higher doses. AU were determined by the manufacturer using the Radio Allergy Sorbant Test (RAST) inhibition assay compared with a reference preparation characterized by skin bioreactivity. $FEV_1$, and Peak Expiratory Flow Rate (PEFR) were measured using a dry spirometer (Vitalograph, Buckingham, England) and a mini-Wright Peak Flow Meter (Clement Clarke International Ltd., London, England) before and 10 minutes after administration of a first dose of 0.15 AU. The procedure was then repeated by doubling the allergen dose until a 25% or greater decrease of $FEV_1$ from baseline was observed, or a maximum allergen dose of 19.2 AU was reached. The provocative dose of allergen causing a 25% $FEV_1$ decrease ($PD_{25}$) was then calculated by interpolation from the cumulative dose-response curve, plotted on semilogarithmic paper.

Study design

The effect of pre-treatment with inhaled NSAID on the bronchial responses to allergen challenge was investigated in three different studies.

In a first study, the effect of pre-treatment with L-ASA on the immediate bronchial allergic response was investigated in a double blind, cross-over study compared to placebo, using a random-number table for randomization. Clinical characteristics of the patients selected for the study according to the above criteria are listed in Table I.

Each patient performed two bronchial challenges within an interval of 4 to 14 days, using a single dose of allergen corresponding to the $PD_{25}$ determined in the preliminary challenge. Before each test, the patients either received an aerosol with 4 ml of L-ASA 180 mg/ml in saline, corresponding to 100 mg/ml of acetyl salicylic acid (Flectadol$^R$, Maggioni-Winthrop S.p.A., Milan, Italy) or a placebo (normal saline) in 15 minutes, given by means of a jet nebulizer (Mod. Soffio, Markos, Monza, Italy) set to an output of 0.27 ml/min. Immediately thereafter, the selected dose of allergen was delivered by a dosimeter. Specific airway resistance (sRaw) was measured during normal breathing using a constant-volume body plethysmograph with a closed bag system to condition air to BTPS (Fenyves & Gut, Basel, Switzerland before and after pretreatment, and at 5, 10, 15, 20, 30, 45 and 60 minutes after the challenge. These measurements were made at least in quintuplicate and the mean was computed. $FEV_1$ was obtained by integration of flows measured with a No. 3 Fleisch pneumotachograph connected to the body plethysmograph. The best value of the first 3 technically satisfactory spirograms was chosen for analysis.

In four separate patients, with comparable clinical characteristics to the previous group, the effect of the two NSAIDs, indomethacin and tenoxicam, on the immediate bronchial response to allergen was investigated. The study protocol was identical to the previous study, except that L-ASA was substituted by a solution of either indomethacin 5 mg/ml or tenoxicam 2 mg/ml. The effect of indomethacin was tested in three, and tenoxicam in one subject.

To investigate the effect of pre-treatment with inhaled L-ASA on the late phase of the asthmatic reaction, two more patients presenting a dual asthmatic response to the preliminary challenge and characterized by the occurrence of a second obstructive response after the resolution of the immediate response, between the fourth and the eighth hour after challenge were studied. The study was conducted according to the previous protocol, except that respiratory function was monitored every 60 minutes up to eight hours after challenge.

Data analysis

Data were expressed as absolute values or as a percentage of baseline values at time zero, i.e. after treatment with the active drug or placebo and immediately before challenge.

Changes of UNW reactivity were measured as doubling doses of UNW $PD_{20}$ compared to placebo, and calculated as $$\log_2 (PD_{20} \text{ after drug}) - \log_2 (PD_{20} \text{ after placebo}).$$

An increase of the $PD_{20}$ by one doubling dose then corresponds to a 100% increase of the cumulative dose of nebulized water causing a 20% $FEV_1$ decrease.

The percentage protective effects on the specific asthmatic response for $FEV_1$ and for sRaw were calculated for each patient according to the formula:

$$((AUC\ \text{placebo} - AUC\ \text{treatment})/AUC\ \text{placebo}) \times 100,$$

where AUC is the area under the time-response curve of the absolute differences from baseline. All data were calculated without knowledge of the randomized treatment.

A two-way analysis of variance and a paired Student's test were used for statistical comparison of normally distributed variables, and the method of the least-significant difference was used for multiple comparisons (see Snedecor and Cochran, Statistical methods. 7th ed. Ames, Iowa University Press, 1980). A level of p of less than 0.05 (two-tailed) was considered significant.

Results

Studies on non-specific bronchial reactivity

Figure 1:
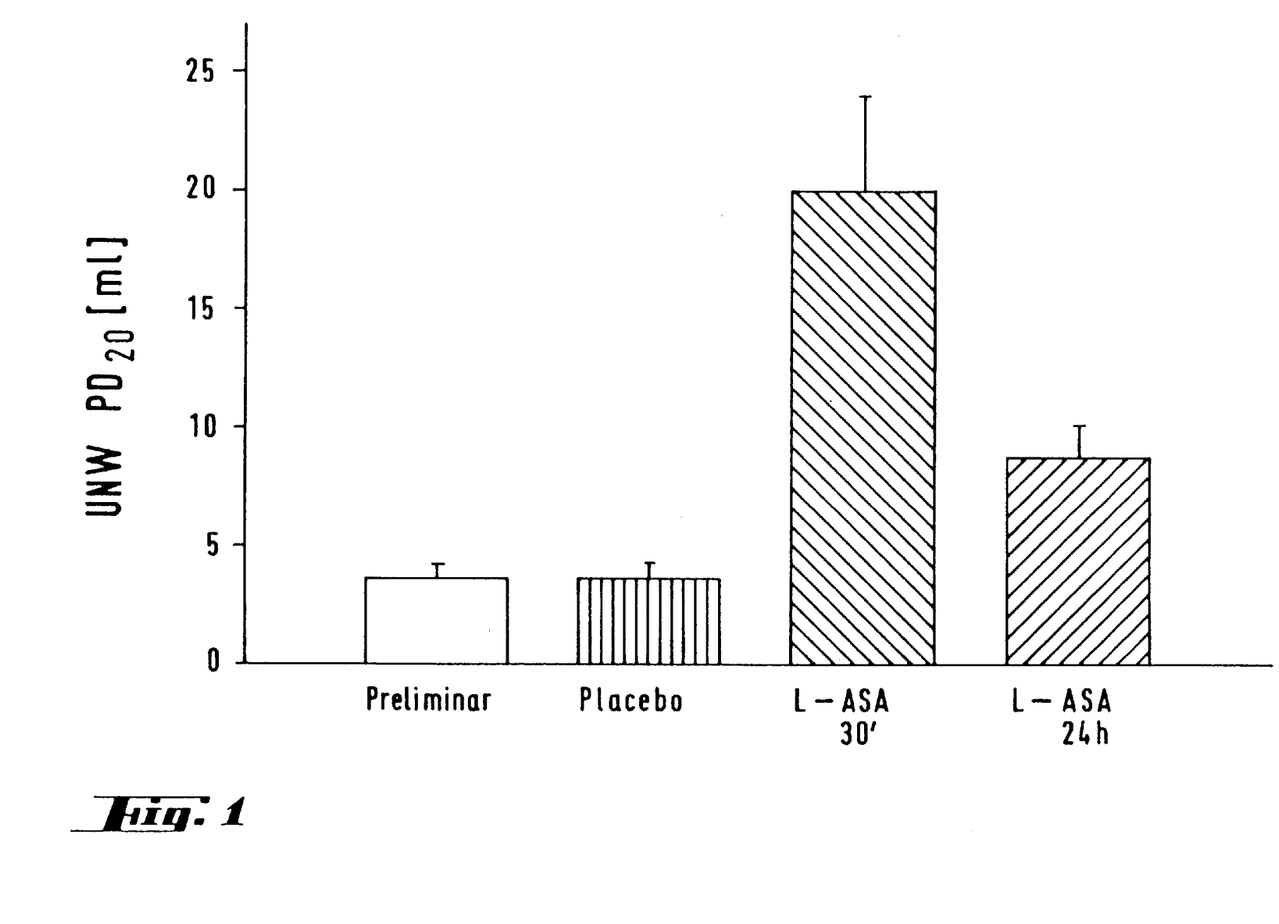
FIG. 1. Effect of inhaled L-ASA (100 mg/ml) on bronchial reactivity to UNW at 30' and 24 hrs after treatment. Data are expressed as M±SE of UNW $PD_{20}$. Clinical characteristics of the study group are reported in table I.

The effect of pre-treatment with L-ASA on UNW-induced bronchoconstriction is shown in FIG. 1. The treatment was well tolerated, and no significant changes of baseline respiratory function parameters were observed on the different study days. The bronchial response to UNW after treatment with placebo was similar to the preliminary day. By contrast the UNW $PD_{20}$ after inhaled L-ASA was markedly increased by 2.42±0.20 doubling doses (M±SE), and continued to be significantly increased compared to placebo even after 24 hours (1.33±0.16 doubling doses).

Figure 2:
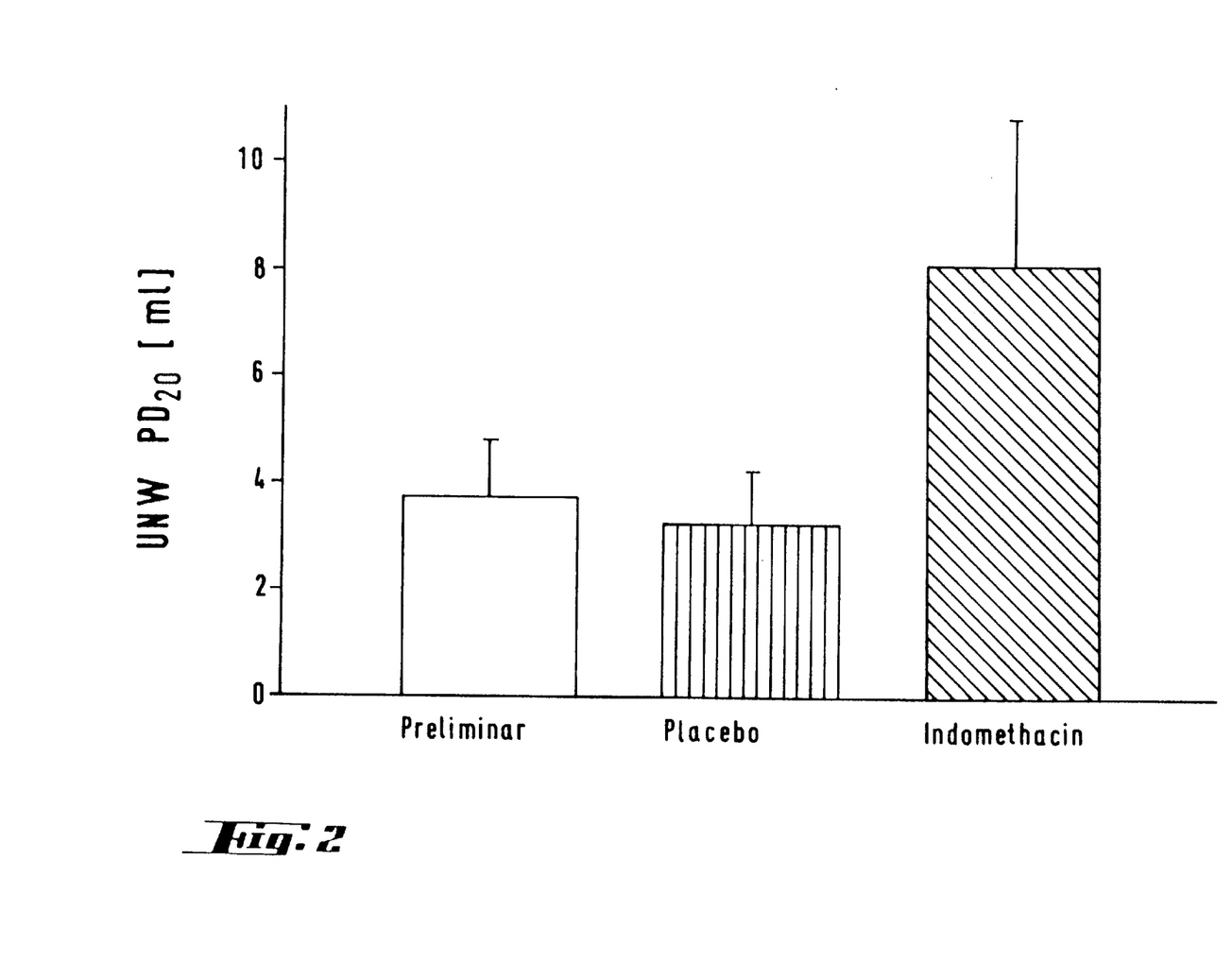
FIG. 2. Effect of inhaled indomethacin (5 mg/ml) on bronchial reactivity to UNW, Clinical characteristics of the study group are reported in table II.

Indomethacin was also generally well tolerated when given by inhalation, and was also found to afford a significant protection against UNW in asthmatics. In the group of 6 patients shown in FIG. 2, UNW $PD_{20}$ rose by 1.2±0.23 doubling doses after treatment with indomethacin 5 mg/mi. In three patients treated with indomethacin 10 mg/ml the UNW $PD_{20}$ rose even higher reaching 3.14±0.23 doubling doses (not shown).

In the pilot study both NSAIDS tenoxicam and ketoprofen were also found to be suitable for administration by inhalation to patients with asthma.

Figure 3:
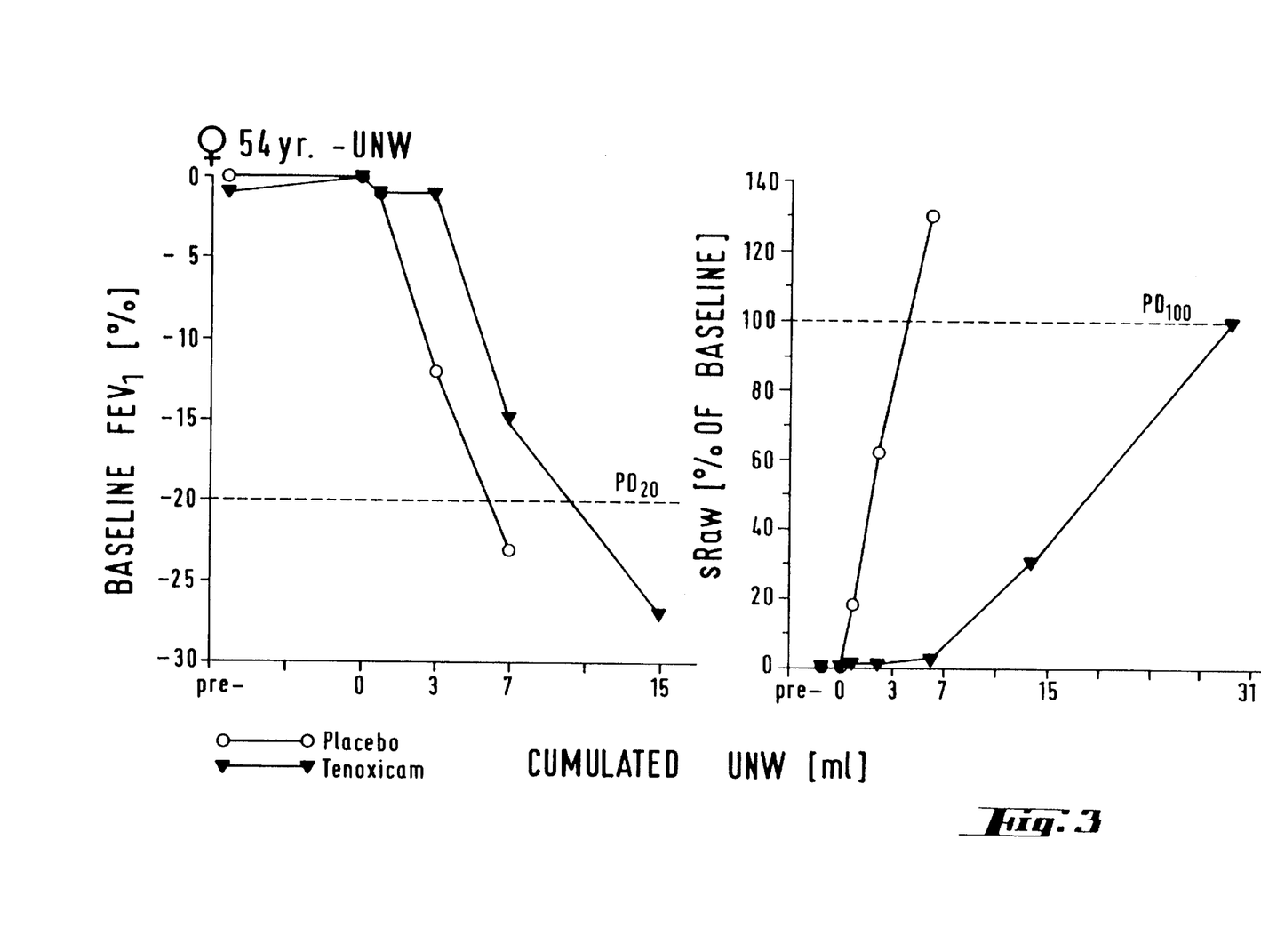
FIG. 3. Effect of inhaled tenoxicam (2 mg/ml) on bronchial reactivity to UNW measured 20' after treatment in a patient with non-allergic asthma.
Figure 4:
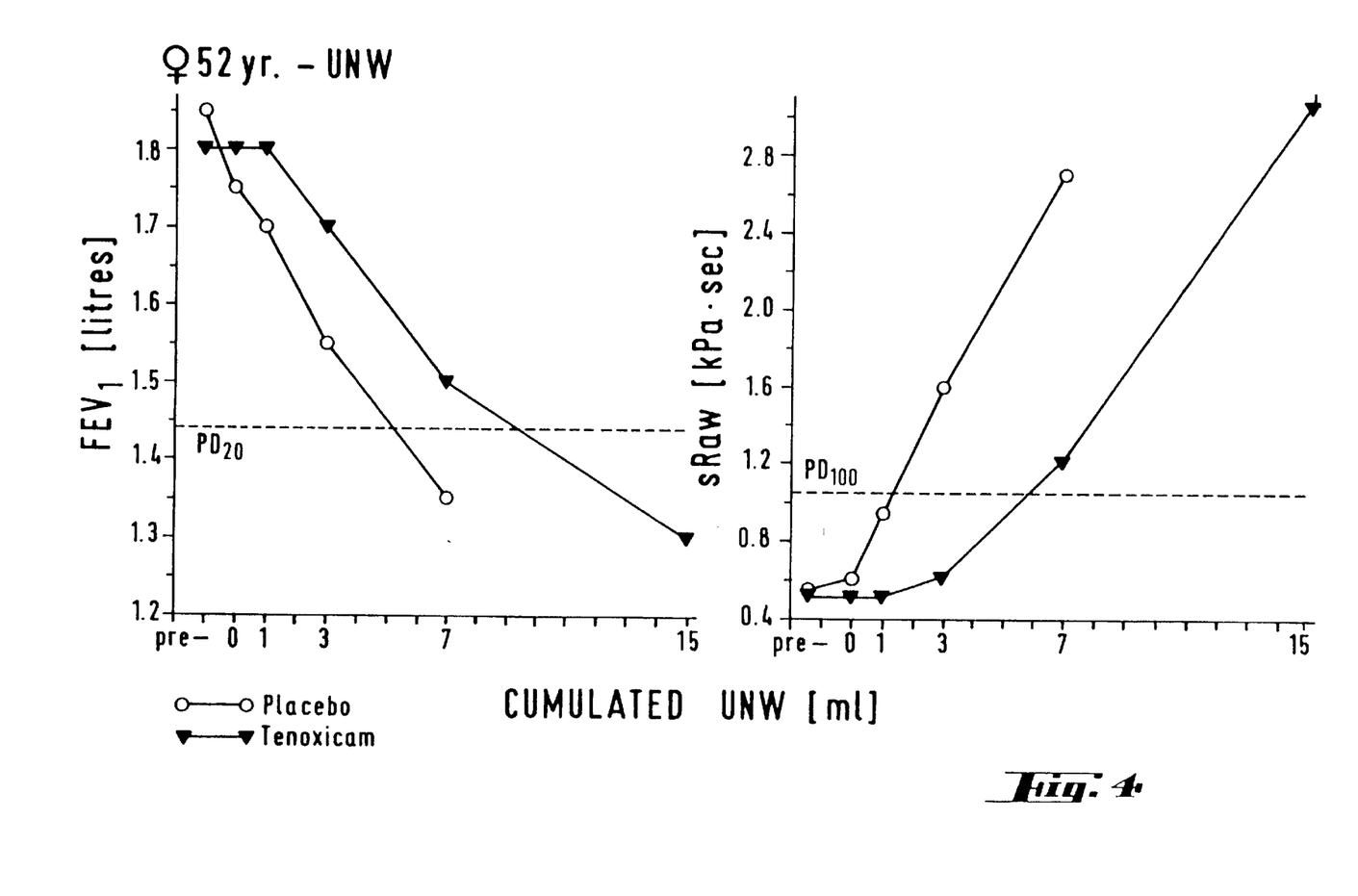
FIG. 4. Effect of inhaled tenoxicam (2 mg/ml) on bronchial reactivity to UNW measured 3 hours after treatment in a patient with non-allergic asthma.
Figure 5:
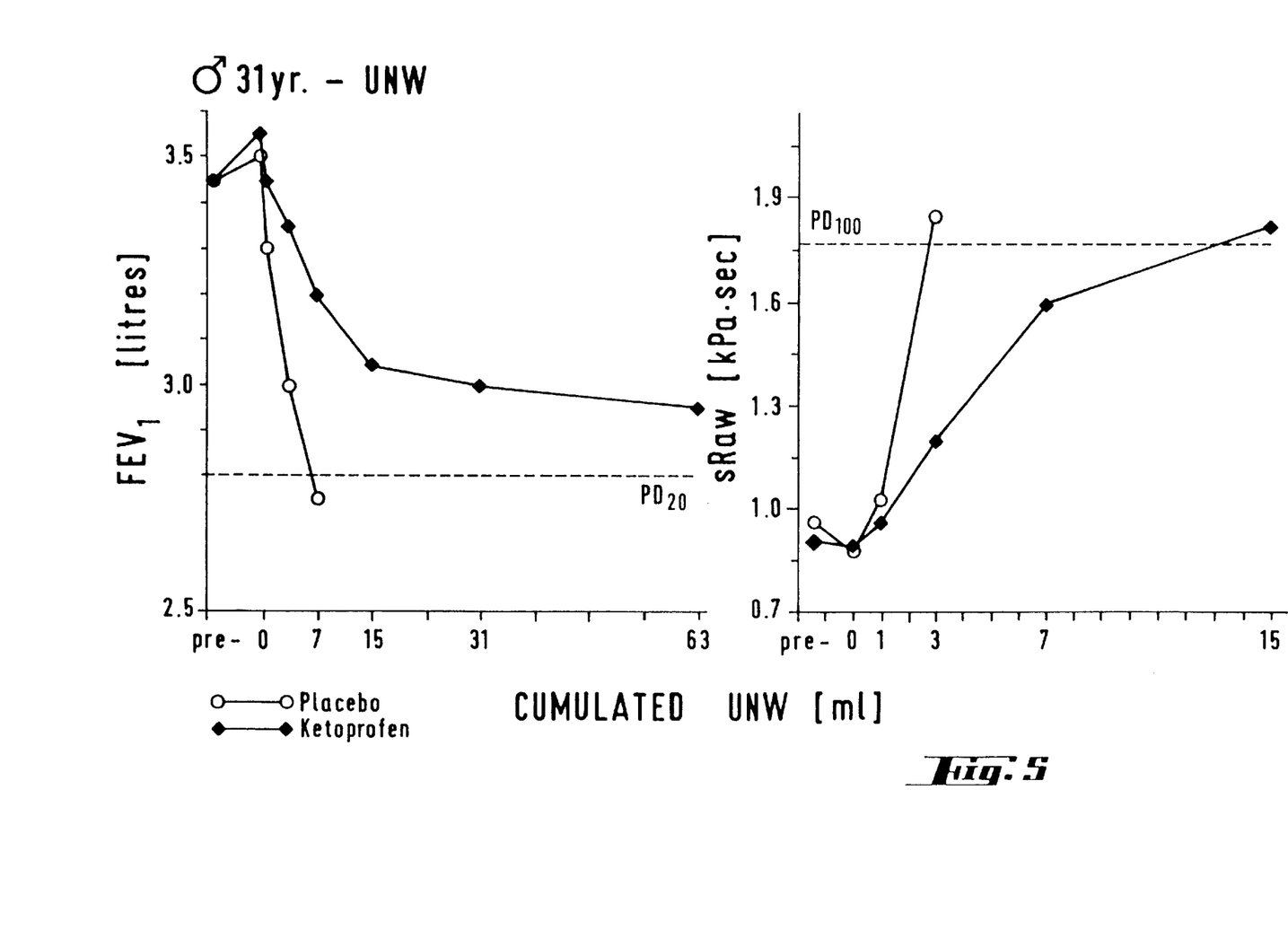
FIG. 5. Effect of inhaled ketoprofen (10 mg/ml) on bronchial reactivity to UNW measured immediately after treatment in a patient with non-allergic asthma (Predicted $FEV_1$ 4.00 l).

The effect of tenoxicam in two patients is shown in FIGS. 3 and 4 in which the UNW test was conducted 20 minutes and 3 hours, respectively, after the inhalation of the drug. Similar results were obtained in a third patient. The effect of ketoprofen in one patient is also shown in FIG. 5.

In the group of 7 patients tenoxicam was also well tolerated when given by inhalation. The protective effects of tenoxicam are shown in Table V. The UNW PD20 rose by less than 1 doubling dose resulting in a modest protection.

In the group of five patients ketoprofen was also generally well tolerated when given by inhalation. The protective effects are shown in Table VI. The UNW PD20 rose by approximately 4 doubling doses. The taste of the solution was rather unpleasant. There was also a slight irritating effect of upper airways (larynx—trachea) after the inhalation of the aerosol. The protection on the average is good although highly variable among subjects.

Studies on allergen challenge

Figure 6:
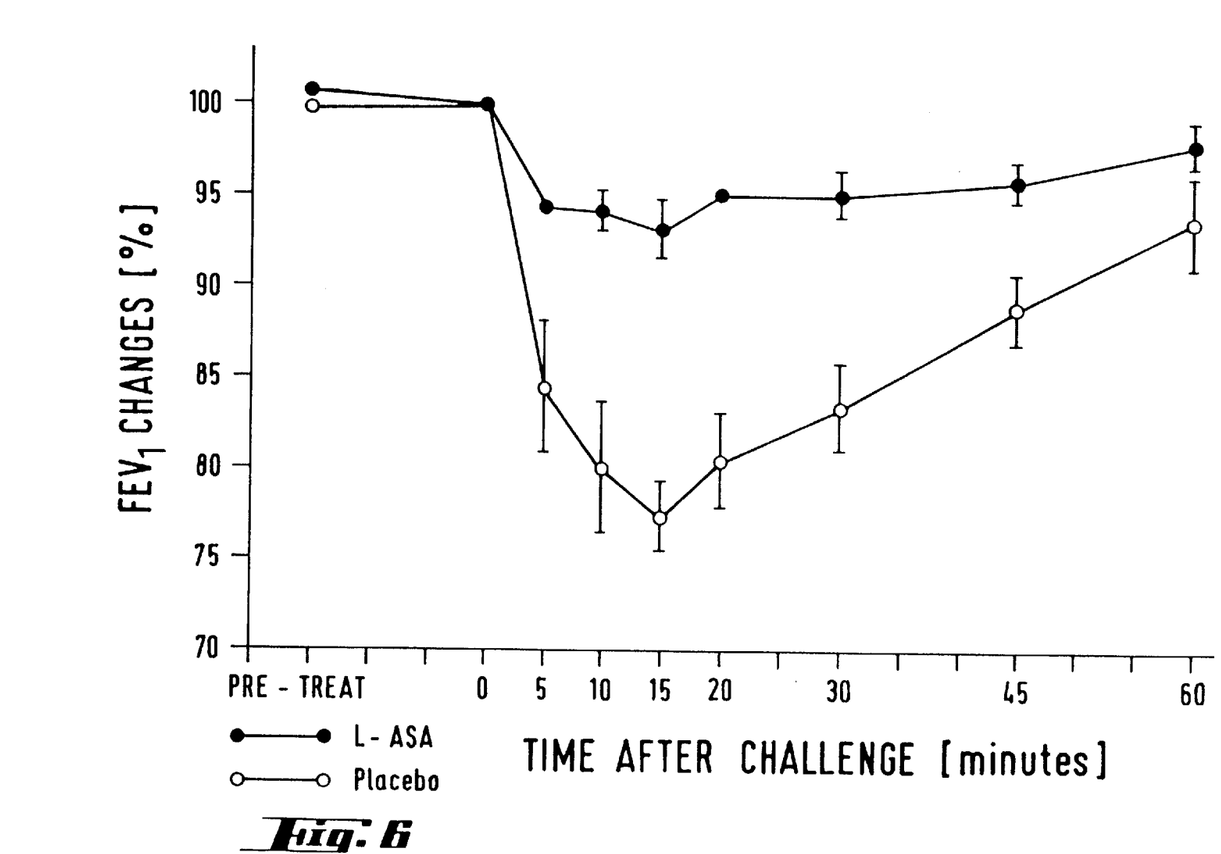
FIG. 6. Time course of $FEV_1$ changes, expressed as percentage of post-treatment value (time 0), after specific allergen challenge. Bars represent mean and SE after inhalation of placebo (unfilled circles) and L-ASA (filled circles). Baseline values (arrow) were 3.90±0.2 l (M±SE) before placebo and 3.95±0.20 before L-ASA. p<0.05 compared to placebo at the same time point, paired t test.
Figure 7:
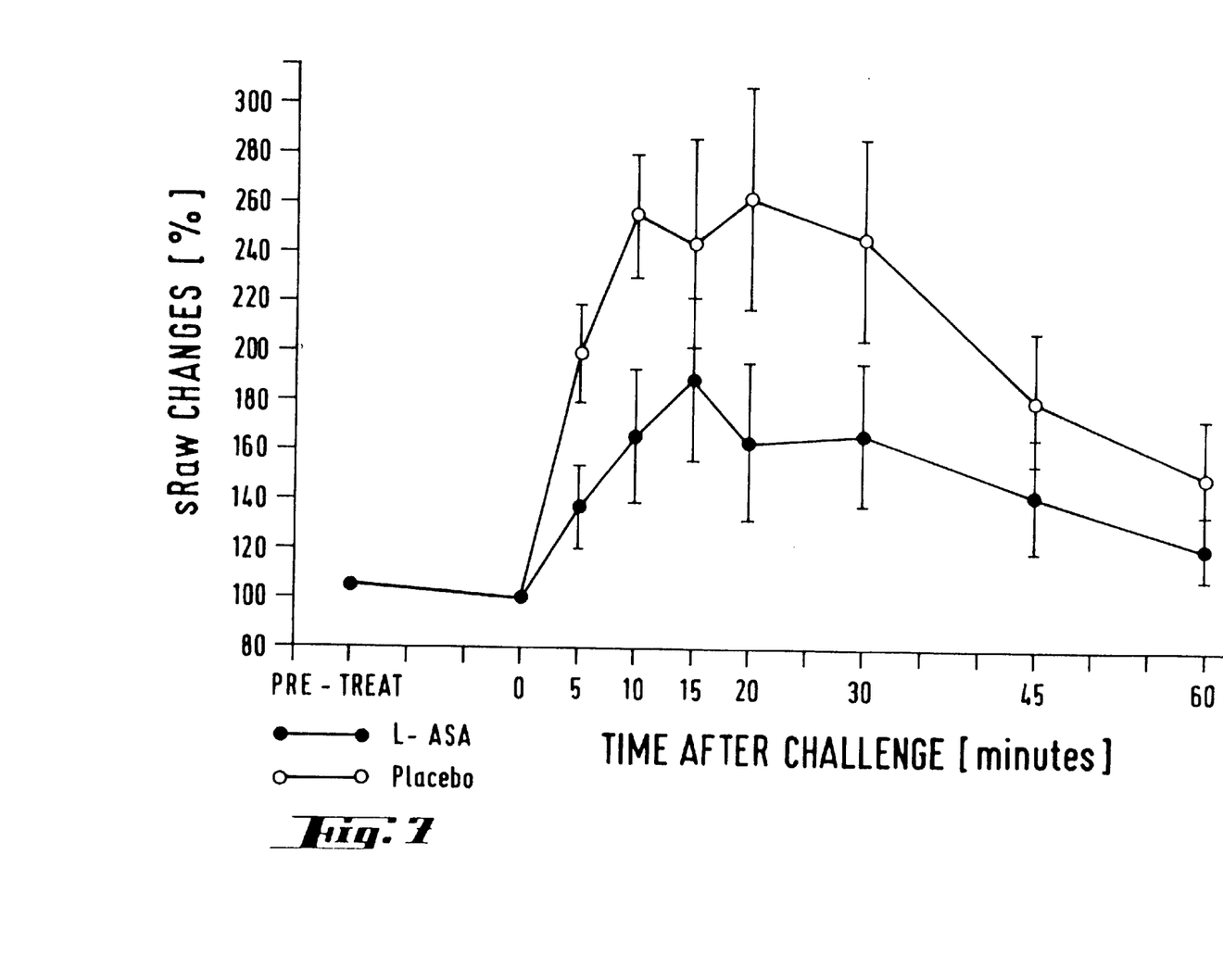
FIG. 7. Time course of sRaw changes, expressed as percentage of post-treatment value (time 0). Baseline sRaw were 0.32±0.32 kPa.s (M±SE) before placebo and 0.35±0.01 before L-ASA, respectively. Symbols as for FIG. 6.

In a first study the effect of pre-treatment with inhaled L-ASA on the bronchial responses to allergen challenge was investigated in 6 patients. Baseline $FEV_1$ on the study days remained similar to those recorded during the preliminary challenge test. Values of $FEV_1$ and sRaw before and immediately after treatment on the study days were also not significantly different. After treatment with placebo, all the patients showed an immediate response which was characterized by a maximum decrease in $FEV_1$ of 24.5±2.3% and a maximum increase in sRaw of 291±35% of baseline values (FIGS. 6 and 7). After treatment with inhaled L-ASA, the bronchial response was markedly reduced, and the mean post-challenge $FEV_1$ changes were significantly lower at every time point when compared with placebo (FIG. 6). The effect on sRaw was somewhat less remarkable, probably due to the greater variability of the response. However, a remarkable difference was seen at 5 and 10 minutes compared to placebo (FIG. 7). The maximum percentage decrease in $FEV_1$ and increase in sRaw (8.6±1.0 and 195±31% of baseline, respectively) were also significantly smaller when as compared with placebo.

The protective activity of L-ASA on the immediate phase of the dual bronchial reaction, between 0 and 60 minutes, was 68±6% when calculated from $FEV_1$ changes, and 56±18% when calculated from the changes of sRaw. None of the patients had clinical manifestations of a late asthmatic response after any of the treatments.

Figure 8:
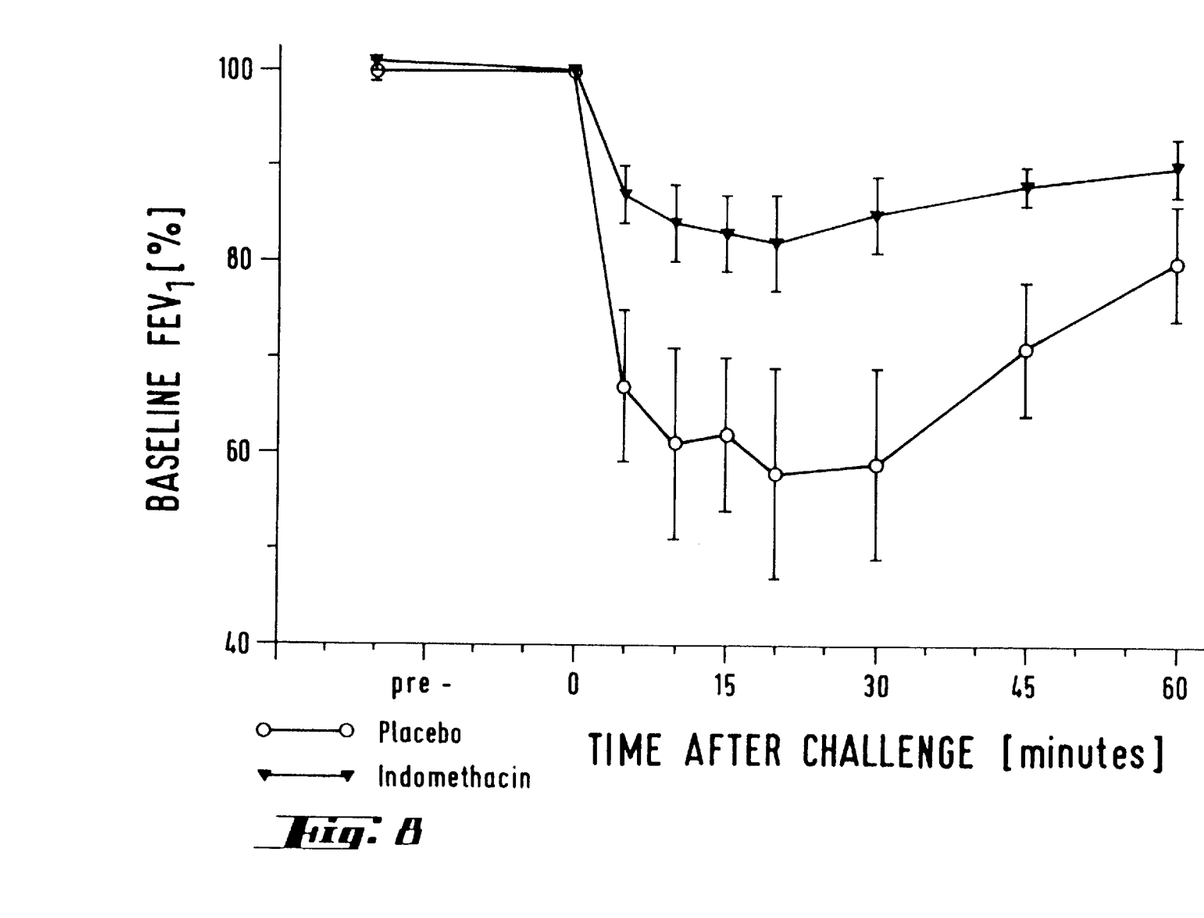
FIG. 8. Effect of the inhalation of indomethacin on the early asthmatic reaction to allergen challenge in a group of three allergic patients, measured as changes of $FEV_1$. Baseline $FEV_1$ in this group was 88±3% of predicted.

The effect of pre-treatment with inhaled indomethacin on the early asthmatic response to allergen in a group of 3 patients is reported in FIG. 8. The drug provided a remarkable reduction of the intensity and the duration of the broncho-obstructive reaction. Maximum $FEV_1$ decrease in this group was 43±11% after placebo and 17±5% after indomethacin. The protection afforded by indomethacin, computed on $FEV_1$ differences from baseline was 51±14%. Also tenoxicam was effective in reducing the early asthmatic reaction in one patient as shown in FIG. 9.

Figure 10:
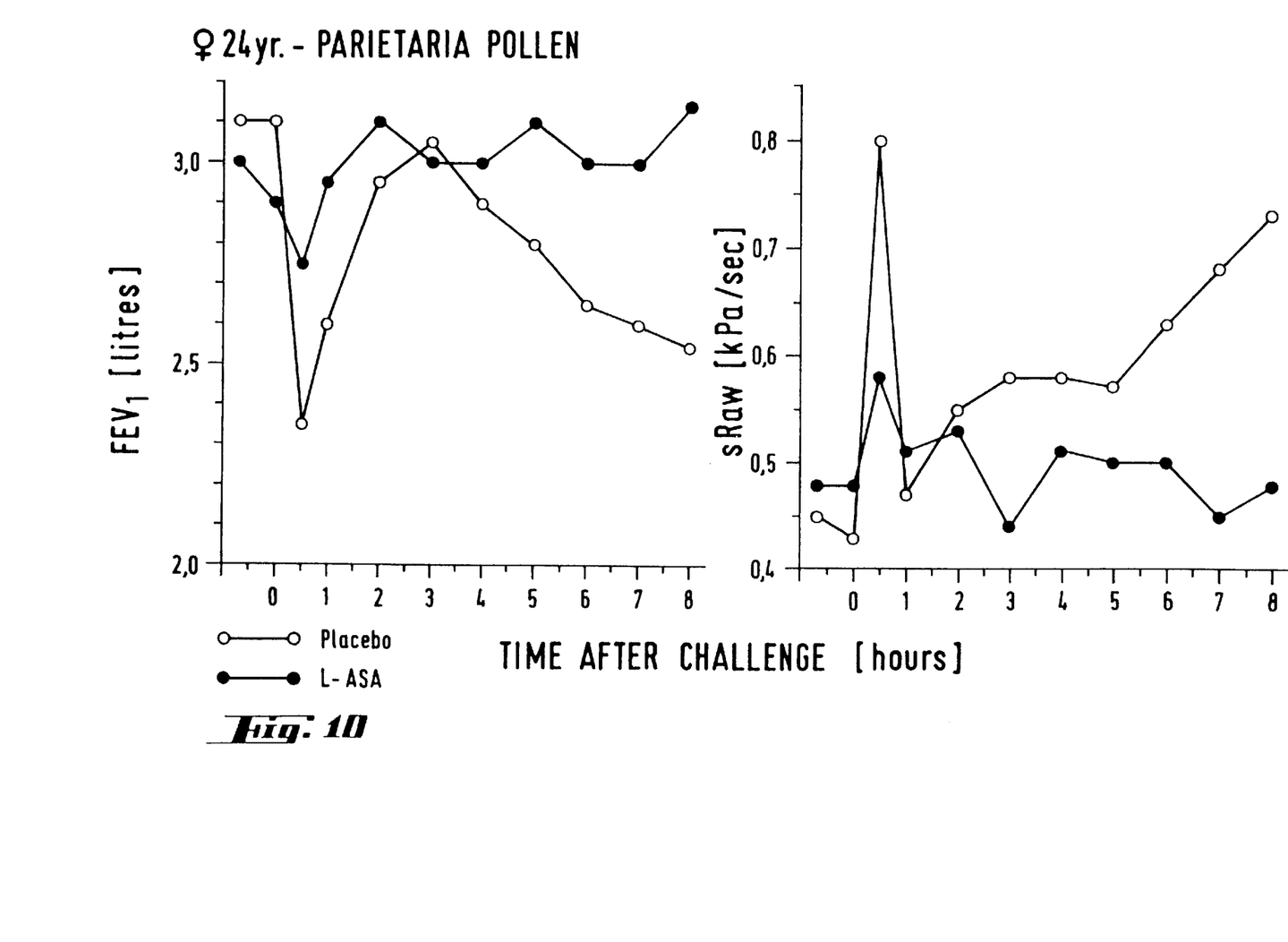
FIG. 10. Effect of inhaled L-ASA on the late asthmatic reaction to allergen challenge in a patient sensitive to pollen (predicted $FEV_1$ 3.49 l), measured as changes of $FEV_1$ (left) and sRaw (right).
Figure 11:
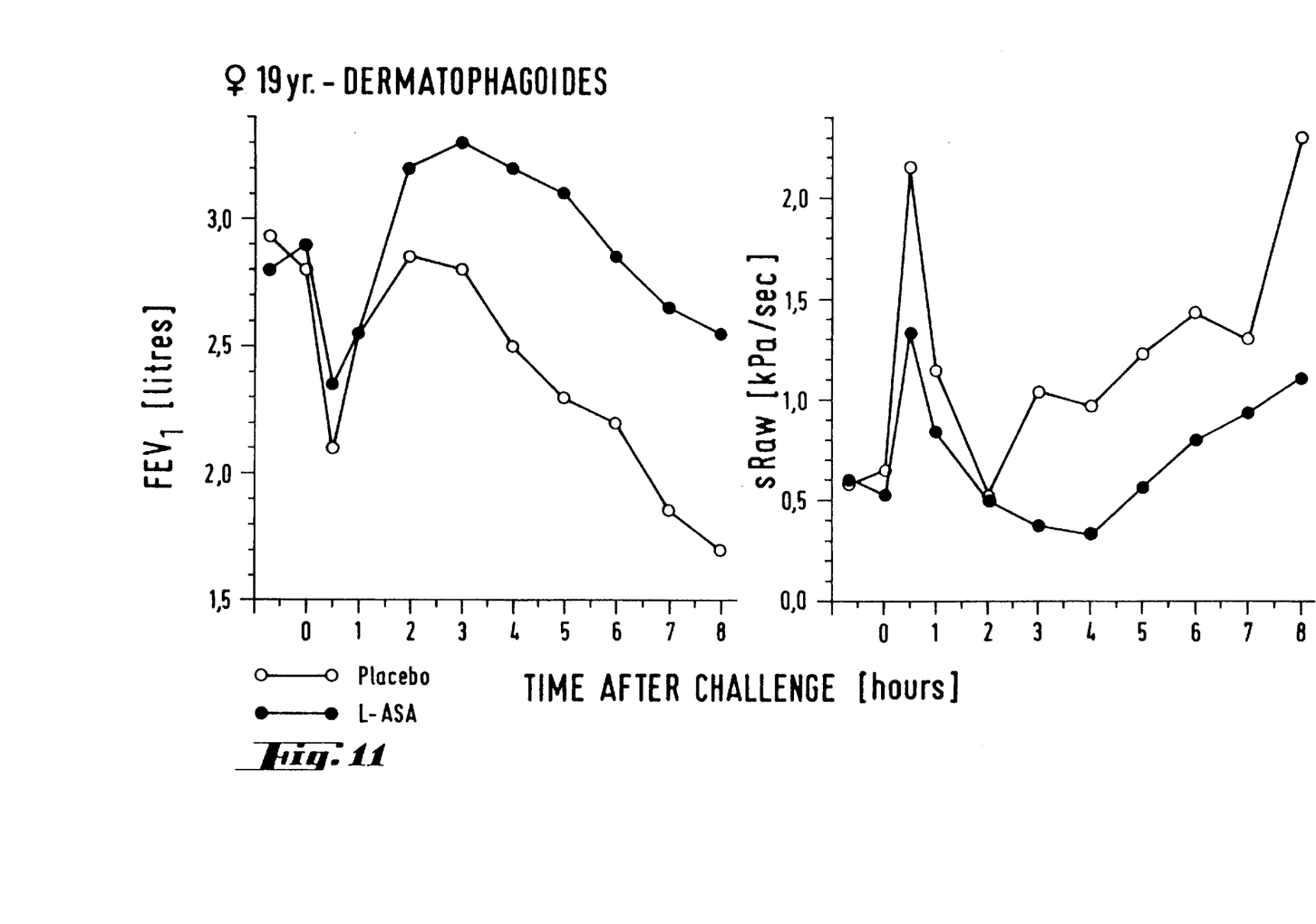
FIG. 11. Effect of inhaled L-ASA on the late asthmatic reaction to allergen challenge in an allergic patient (predicted $FEV_1$ 3.37 l), measured as changes of $FEV_1$ (left) and sRaw (right).

None of the subjects included in the studies above had a late asthmatic reaction to allergen challenge. To evaluate the effect of inhaled NSAIDs on this phenomenon, two other patients showing a dual asthmatic reaction after the preliminary challenge were selected. The effect of pre-treatment with L-ASA or placebo on the allergen-induced reaction in these subjects is shown in FIGS. 10 and 11. In both subjects the late phase of the reaction was markedly attenuated after treatment with inhaled L-ASA.

Discussion

These data clearly show that these problems of high oral doses, resulting in systemic side-effects, can be overcome by administration of NSAIDs by inhalation. In fact, they indicate that the inhalation of a variety of NSAIDs is able to inhibit the bronchial response to non-specific and specific bronchial stimuli in asthmatics. The inhalatory route is effective not only in reducing the side-effects in other organs which are bypassed by the topical treatment, but also in increasing the local activity of the drugs. The inhalatory route also takes advantage of a delayed drug metabolism, revealing the surprisingly long-lasting effect of inhaled L-ASA on UNW-induced bronchospasm (FIG. 1).

It is also interesting to remark that the antireactive effect is not limited to ASA, but is also exerted by others NSAIDs, such as indomethacin, which affect cyclooxygenase metabolism by different mechanisms. It is particularly noteworthy that a significant inhibition of UNW- and allergen-induced responses was observed after inhalation of indomethacin, which in controlled studies has previously been shown to be ineffective on the bronchial response to UNW (J Allergy Clin Immunol 1987, 79:503; and J Allergy Clin Immunol 1987, 79:678–683) and to allergen challenge (J Appl Physiol 1989, 66:578–583; and Rev Respir Dis 1990, 141:1441–1445) after oral administration. Similarly, it is known that another anti-reactive drug, furosemide, is only effective on bronchial responses when given by inhalation and not systemically (Pulmonary Pharmacology 1989, 1:187–191). These data thus stress the importance of the inhalatory route in revealing the therapeutic success of these drugs.

Finally, it is of particular interest that we have observed a good protective effect of inhaled L-ASA also on the late phase of the asthmatic response to allergen (FIGS. 10 and 11).

BRIEF DESCRIPTION OF THE DRAWINGS

FIG. 9. Effect of the inhalation of tenoxicam on the early asthmatic reaction to allergen challenge in a patient sensitive to grass pollen ($FEV_1$ predicted 4.0 l) measured as changes of $FEV_1$ (left) and sRaw (right).

TABLE I

Effect of inhaled L-ASA on UNW-induced bronchial reactions. (Patients' characteristics)

| N. | Sex | Age | $FEV_1$ liter | % pred | ALLERGY[a] | THERAPY[b] |
|---|---|---|---|---|---|---|
| 1 | M | 34 | 3.85 | 94 | DP | B2 + CS |
| 2 | M | 24 | 3.18 | 78 | — | B2 |
| 3 | F | 39 | 2.47 | 98 | — | B2 + CS |
| 4 | F | 19 | 3.08 | 100 | GR | B2 |
| 5 | F | 35 | 2.10 | 75 | — | B2 + CS |
| 6 | F | 40 | 2.32 | 90 | GR | B2 |
| 7 | M | 18 | 3.29 | 81 | — | B2 |

[a]DP: Dermatophagoides, GR: Grass pollen
[b]B2: inhaled beta2-agonist, CS: inhaled steroids

TABLE II

Effect of inhaled indomethacin on UNW-induced bronchial reactions. (Patients' characteristics)

| N. | Sex | Age | $FEV_1$ liter | % pred | ALLERGY[a] | THERAPY[b] |
|---|---|---|---|---|---|---|
| 1 | F | 60 | 2.12 | 87 | — | B2 + CS |
| 2 | M | 20 | 3.95 | 101 | DP | B2 |
| 3 | F | 40 | 2.15 | 84 | — | B2 |
| 4 | M | 25 | 3.33 | 85 | — | B2 + CS |
| 5 | M | 20 | 4.04 | 98 | — | B2 + CS |
| 6 | F | 18 | 2.55 | 88 | GR | B2 + CS |

[a]DP: Dermatophagoides, GR: Grass pollen
[b]B2: inhaled beta2-agonist, CS: inhaled steroids

TABLE III

Effect of inhaled tenoxicam on UNW-induced bronchial reactions (Patients characteristics)

| N. | Sex | Age | $FEV_1$ liter | % pred | ATOPY | THERAPY[b] |
|---|---|---|---|---|---|---|
| 1 | M | 25 | 3.32 | 83.5 | — | B2 + CS |
| 2 | M | 43 | 3.50 | 110 | GR | B2 + CS |
| 3 | M | 18 | 5.0 | 111 | GR | B2 + CS |
| 4 | M | 35 | 3.66 | 88.5 | — | B2 + CS |
| 5 | F | 42 | 2.60 | 101 | — | B2 + CS |
| 6 | M | 19 | 4.13 | 101 | GR | B2 + CS |
| 7 | F | 60 | 3.20 | 92 | — | B2 + CS |

[a]DP: Dermatophagoides, GR: Grass pollen
[b]B2: inhaled beta2-agonist, CS: inhaled steroids

TABLE IV

Effect of inhaled ketoprofen on UNW-induced bronchial reactions (Patients characteristics)

| N. | Sex | Age | $FEV_1$ liter | % pred | ATOPY | THERAPY[b] |
|---|---|---|---|---|---|---|
| 1 | M | 25 | | 83.5 | — | B2 + CS |
| 2 | M | 20 | | 90 | GR | B2 + CS |
| 3 | M | 45 | | 98 | — | B2 + CS |
| 4 | F | 61 | | 90.6 | — | B2 + CS |
| 5 | M | 42 | | 114 | GR | B2 + CS |

[a]DP: Dermatophagoides, GR: Grass pollen
[b]B2: inhaled beta2-agonist, CS: inhaled steroids

TABLE V

Tenoxicam UNW PD20 (ml)

| | Preliminary | Placebo | Tenoxicam 5 ml-4 mg/ml |
|---|---|---|---|
| 1 | 3.7 | 3.5 | 6 |
| 2 | 8.2 | 8.0 | 15 |
| 3 | 2.0 | 1.5 | 9 |
| 4 | 5.0 | 4.0 | 6 |
| 5 | 2.5 | 3.5 | 5 |
| 6 | 8.0 | 6.75 | 6.25 |
| 7 | 4.8 | 6.0 | 7.7 |
| x | 4.9 | 4.75 | 7.85 |
| SD | 2.4 | 2.25 | 3.4 |

TABLE VI

| | Ketoprofen UNW PD20 (ml) | | |
| --- | --- | --- | --- |
| | Preliminary | Placebo | Ketoprofen 7 ml-7.14 mg/ml |
| 1 | 2.5 | 3.5 | 59 (PD 15) |
| 2 | 4.5 | 7.5 | 23 |
| 3 | 6.2 | 6.2 | 59 |
| 4 | 4.0 | 4.8 | 10 |
| 5 | 2.B | 2.5 | 6 |
| x | 4.0 | 4.9 | 31.4 |
| SD | 1.48 | 2.0 | 25.9 |

I claim:

1. A composition comprising a non-steroidal anti-inflammatory drug and a propelling agent.

2. The composition of claim 1, wherein said non-steroidal anti-inflammatory drug is acetylsalicylic acid.

3. The composition of claim 1, wherein said non-steroidal anti-inflammatory drug is indomethacin.

4. The composition of claim 1, wherein said non-steroidal anti-inflammatory drug is ketoprofen.

5. The composition of claim 1, wherein said non-steroidal anti-inflammatory drug is tenoxicam.

6. The composition of claim 1, wherein said propelling agent is a fluorochlorohydrocarbon, a fluorinated hydrocarbon, dimethyl ether, propane, butane, nitrogen, carbon dioxide, or nitrous oxide.

7. The composition of claim 1, which is a pharmaceutical composition.

8. The composition of claim 1, wherein said composition is an aqueous or aqueous-organic suspension or solution.

9. An inhalant composition comprising a mixture of powders with microfine drugs.

10. A device for dispensing a pharmaceutical composition, wherein said device comprises an inhaler containing said pharmaceutical composition comprising a non-steroidal anti-inflammatory drug and a propelling agent.

11. The device of claim 10, wherein said device aerosolizes said pharmaceutical composition during dispensing.

12. A method of treating asthma, which comprises administering by inhalation to a host in need thereof a nonsteroidal anti-inflammatory drug in an amount effective to treat asthma.

13. The method of claim 12, wherein said anti-inflammatory drug is acetylsalicylic acid.

14. The method of claim 12, wherein said anti-inflammatory drug is indomethacin.

15. The method of claim 12, wherein said anti-inflammatory drug is ketoprofen.

16. The method of claim 12, wherein said anti-inflammatory drug is tenoxicam.

17. The method of claim 13, wherein the amount effective is selected from a range of 4 ml to 5 ml of 100 mg/ml acetylsalicylic acid.

18. The method of claim 14, wherein the amount effective is selected from a range of 5 ml of 5 mg/ml indomethacin to 5 ml of 10 mg/ml indomethacin.

19. The method of claim 15, wherein the amount effective is selected from a range of 5 ml of 10 mg/ml ketoprofen to 7 ml of 7.14 mg/ml ketoprofen.

20. The method of claim 16, wherein the amount effective is selected from a range of 5 ml of 2 mg/ml tenoxicam to 5 ml of 4 mg/ml tenoxicam.

* * * * *